(12) United States Patent
Fichet

(10) Patent No.: US 8,082,111 B2
(45) Date of Patent: Dec. 20, 2011

(54) OPTICAL EMISSION SPECTROSCOPY QUALITATIVE AND QUANTITATIVE ANALYSIS METHOD

(75) Inventor: Pascal Fichet, Poissy (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 893 days.

(21) Appl. No.: 12/083,664

(22) PCT Filed: Oct. 5, 2006

(86) PCT No.: PCT/FR2006/050995
§ 371 (c)(1), (2), (4) Date: Apr. 16, 2008

(87) PCT Pub. No.: WO2007/045782
PCT Pub. Date: Apr. 26, 2007

(65) Prior Publication Data
US 2009/0259410 A1    Oct. 15, 2009

(30) Foreign Application Priority Data
Oct. 17, 2005  (FR) ..................... 05 53145

(51) Int. Cl.
*G06F 19/00*    (2006.01)
(52) U.S. Cl. ............... 702/23; 702/28; 702/30; 356/318

(58) Field of Classification Search ............. 702/22–28, 702/30–32; 356/318, 326
See application file for complete search history.

(56) References Cited

U.S. PATENT DOCUMENTS

| | | | |
|---|---|---|---|
| 5,446,538 A * | 8/1995 | Noll | 356/318 |
| 6,753,957 B1 | 6/2004 | Graft et al. | |
| 2005/0024638 A1 | 2/2005 | Lacour et al. | |

OTHER PUBLICATIONS

Fichet, Pascal et al., "Analysis by Laser-Induced Breakdown Spectroscopy of Complex Solids, Liquids, and Powders with Echelle Spectrometer," Applied Optics, Vo. 42, No. 30, pp. 6029-6035 (Oct. 20, 2003).*

Pascal Fichet, et al., "Analysis by laser-induced breakdown spectroscopy of complex solids, liquids, and powders with an echelle spectrometer," Applied Optics, vol. 42, No. 30, pp. 6029-6035 (Oct. 20, 2003).

* cited by examiner

*Primary Examiner* — Manuel L Barbee
(74) *Attorney, Agent, or Firm* — IM IP Law PLLC; C. Andrew Im

(57) ABSTRACT

The invention relates to a method for the qualitative and quantitative analysis of samples by optical emission spectroscopy with laser excitation (18), using a database created on single-element aqueous solutions all having the same pure element concentration, this database containing, for each element, the wavelengths of the emission lines and their respective intensities.

13 Claims, 1 Drawing Sheet

OPTICAL EMISSION SPECTROSCOPY QUALITATIVE AND QUANTITATIVE ANALYSIS METHOD

RELATED APPLICATIONS

This application is a §371 from PCT/FR2006/050995 filed Oct. 5, 2006, which claims priority from FR 05 53145 filed Oct. 17, 2005, each of which is herein incorporated by reference in its entirety.

FIELD OF THE INVENTION

The present invention concerns a method for the qualitative and quantitative analysis of any type of single- or multi-element sample, from a database created using optical emission spectroscopy on pure elements in solution.

BACKGROUND OF THE INVENTION

It is known, when analyzing any type of material, to use optical emission spectroscopy on laser-induced plasma. This elementary analytical technique is known as LIBS (Laser-Induced Breakdown Spectroscopy). The principle is to analyze the lines emitted by a material to be analyzed as a function of their intensity. This analysis is generally done line by line, which is relatively painstaking. When a method of this type is used without access to specific databases, it is impossible to study the correlation of the various elements present in the sample with one another. In fact, the existing databases, for example the databases like those provided by the American agency NIST (National Institute of Standards and Technology), contain results recorded with different measuring devices and in different formats; therefore, these databases cannot be used to perform intensity comparisons between several elements, since not all measuring devices have the same influence on the readings taken.

Furthermore, when wishing to use a method like LIBS for quantitative analysis, it may be necessary to create a calibration curve for the detection device used, in order to compensate for any influence this device may have on the measurements obtained. The known methods for obtaining these calibration curves are generally such that the curves depend on the matrix used, i.e. a liquid, solid or gaseous matrix, and it is therefore necessary to recalculate them for each matrix analyzed. Thus, if a calibration curve is created for solutions, i.e. for a liquid matrix, this curve is not necessarily valid for measurements performed on gaseous or solid samples.

Methods for eliminating these matrix effects have been proposed, but these methods are based on physical interpretations of the results and do not account for the problems associated with testing, such as spectral saturation or simultaneous analyses of major and trace elements.

It is also known to create a database on liquid solutions and to use this database for the qualitative analysis of any type of sample, though not for quantitative analysis.

SUMMARY AND OBJECTION OF THE INVENTION

The invention therefore concerns a method of analysis that eliminates at least one of these drawbacks.

The invention concerns a method for the qualitative and quantitative analysis of any type of single- or multi-element sample by optical emission spectroscopy with laser excitation, using a database created on single-element aqueous solutions all having the same pure element concentration, this database containing, for each element, the wavelengths of the emission lines and their respective intensities, the method comprising the following steps:

calculating, from the database, inter-element coefficients between all of the elements of interest, i.e., those likely to be found together in a sample, an inter-element coefficient corresponding to the ratio between the intensities of two lines from two different elements. Such a coefficient is represented by the formula $$coefficient_{(i,j)}(\alpha/\beta) = \frac{I_i(\alpha)}{I_j(\beta)},$$

where $I_i(\alpha)$ and $I_j(\beta)$ are the respective intensities of the line $\alpha$ in the element i and the line $\beta$ in the element j, these intensities being obtained from the database next, performing an analysis of the sample using optical emission spectroscopy to determine at least some of the various emission lines present and their intensities then determining, from the emission spectrum, the elements present in the sample, and lastly, using the inter-element coefficients and the intensities of the lines detected to quantitatively calculate the respective concentrations of the various elements identified previously during the qualitative analysis.

This calculation consists of applying the following formula:

$$c_1 + \sum_i coefficient_{(1,i)}(\alpha_i/\beta_i) * \frac{J_i(\beta_i)}{J_1(\alpha_i)} * c_1 = 100,$$

in which $c_1$ represents the mass percentage concentration of an element of the sample chosen as a reference element, and the terms of the sum represent the concentrations of the other elements of the sample expressed as a function of the concentration $c_1$, the inter-element coefficients, and the intensities $J_i$ measured during the analysis of the sample. The inter-element coefficients are normalized so as to be usable with one another. In this formula, $J_i(\beta_i)$ and $J_1(\alpha_1)$ represent the respective intensities of any line $\beta_i$ in the element i and any line $\alpha_i$ in the element 1, these intensities being measured when the sample is analyzed, during which analysis the lines are detected.

The formula $$c_1 + \sum_i coefficient_{(1,i)}(\alpha_i/\beta_i) * \frac{J_i(\beta_i)}{J_1(\alpha_i)} * c_1 = 100$$

is equivalent to $$\sum_i c_i = 100,$$

where $c_i$ is the mass percentage concentration of the element i.

This concentration $c_i$ may be written as a function of the concentration $c_l$ of a given element, and as a function of the inter-element coefficients between the element i and the element 1.

In essence, the inter-element coefficients are such that we have $$\frac{J_1(\alpha_i)}{J_i(\beta_i)} = \frac{c_1}{c_i} * coefficient_{(1,i)}(\alpha_i/\beta_i).$$

Thus, $$c_i = coefficient_{(1,i)}(\alpha_i/\beta_i) * \frac{J_i(\beta_i)}{J_1(\alpha_i)} * c_1.$$

DETAILED DESCRIPTION OF THE EMBODIMENTS

Figure 1:
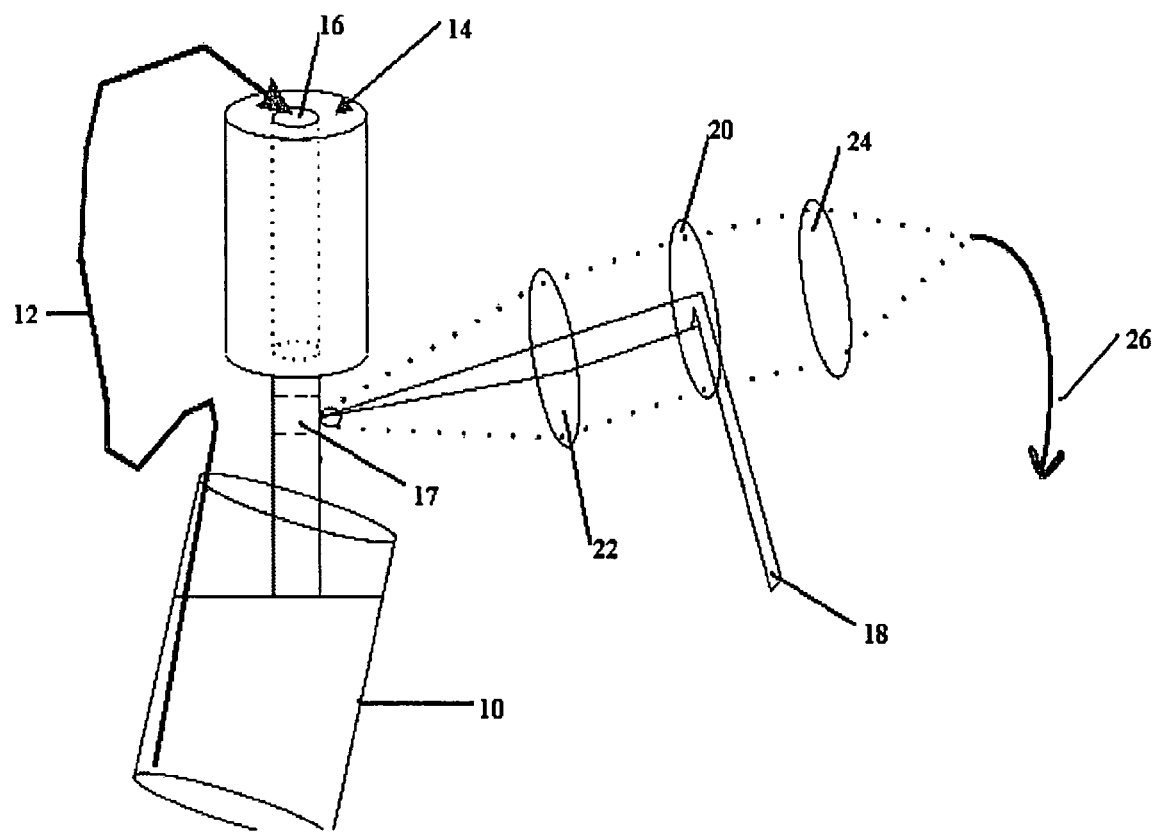
FIG. 1 is a schematic drawing of an exemplary apparatus for performing the qualitative and quantitative analysis in accordance with an embodiment of the present invention.

The database used by the invention is created specifically for this analysis. To do this, a method of analysis by optical emission spectroscopy with laser excitation is used, which means that a laser beam is used to produce a plasma, also called a spark, in a sample, which in this case is a pure element in solution. Once transformed into plasma, the element emits a light spectrum composed of lines of different wavelengths. Analyzing this spectrum makes it possible to learn the composition of the element. Once the pure elements have been analyzed, the wavelengths of the various emission lines and their intensities are stored in a data file in electronic format, so as to constitute the database. The data are sorted in order of increasing or decreasing intensity. The results obtained are like those presented in Table I below.

The left column indicates the wavelengths of the various lines of manganese, and the right column indicates the corresponding intensities. The table is sorted in order of decreasing intensity in this example.

TABLE I

File of the lines of Manganese (Mn)

| Wavelength (nm) | Intensity (ua) |
|---|---|
| 257,604 | 43274 |
| 294,914 | 36370 |
| 260,563 | 33743 |
| 259,369 | 29684 |
| 403,071 | 20694 |
| 403,301 | 17819 |
| 293,924 | 15594 |
| 293,297 | 14735 |
| 403,442 | 11490 |
| 344,194 | 10700 |
| 279,474 | 9749 |
| 347,425 | 7483 |
| 279,816 | 7057 |
| 262,565 | 6150 |
| 346,026 | 5792 |
| 404,127 | 5664 |
| 280,099 | 5027 |
| 356,949 | 4434 |
| 348,289 | 4362 |
| 380,671 | 3775 |

The measurements shown in this table are performed on single-element solutions, all having the same concentration.

It is known that in emission spectroscopy, particularly plasma emission spectroscopy, the emission lines can be described by the formula $I_i = Kc_i Me^{-E/kT}$, in which K is a factor that accounts for the collection of the spectroscopic data of the line in question, in the form of a device function, M is the quantity of ablated mass, and $e^{-E/kT}$ represents the temperature of the plasma at thermodynamic equilibrium.

This relation shows that the optical emission is sensitive to matrix effects, by taking the ablated mass into account. Thus, the fact that the database is created from single-element solutions of the same concentration makes it possible to use the coefficients for any type of matrix, particularly for a solid matrix.

Moreover, the fact that this base is created from single-element solutions also makes it possible to create a relatively complete database, i.e. one that contains a great deal of information. In fact, it is possible to have access to solutions for a large number of chemical elements, and thus to perform measurements for all of these elements.

The database is a function of the equipment used, particularly the spectral range and the response time of the detection device. It is therefore necessary to make sure, during the acquisition of the data, to optimize this equipment and to use the same device for all the elements of a database. If different devices are used, it is necessary, for an aqueous solution of the same concentration, to be able to reproduce similar experimental conditions (the nature of the laser, the energy, the response of the spectrometer) and to obtain a passage coefficient, i.e. a factor for normalizing the measurements as a function of the detection device used.

If the pure elements do not all have the same concentration when the data is acquired, it is necessary to add the observed values to values corresponding to a preset pure element concentration that is identical for all of the elements. The fact that this identical concentration is provided and the fact that all of the analyses are performed on elements located in the same matrix, i.e. a liquid matrix, makes it possible to eliminate the matrix effects and to use the results in the database to analyze any type of sample. Thus, the sample to be analyzed is in the liquid, solid or gaseous phase.

During the generation of the database, it is also necessary to make sure that no emission lines have been self-absorbed. In essence, when the pure element concentration of a solution is too high, certain lines can disappear, and therefore cannot be measured. This self-absorption may alter the precision of the quantitative analysis since, in certain cases, it may be necessary to obtain values for all of the lines in order to calculate the concentration of one of the elements of the sample to be analyzed. Thus, in one embodiment of the invention, the pure element concentrations of the solutions used to create the database are lower than a predetermined value, preferably 0.5% by mass, in order to prevent a self-absorption of the lines that would alter the precision of the quantitative analysis.

When the measurements on the spectrum of the sample to be analyzed are performed, the detection device used may become saturated. In that case, all of the lines that have a real intensity higher than the saturation threshold are measured with an intensity equal to that saturation threshold. This can alter the quantitative analysis, producing false measurements for certain lines. To eliminate this drawback, in one embodiment of the invention, when the intensity of at least one line of the emission spectrum of the sample has reached the saturation threshold of the detection device, the real intensity of this line is reconstructed as a function of the intensities of the other lines belonging to the same element and as a function of pre-calculated intra-element coefficients from the database.

An intra-element coefficient is the equivalent of the inter-element coefficients, but for a single element. It corresponds to the ratio of the intensities of two lines of the same element, represented by the formula $$coefficient_i(\alpha/\beta) = \frac{I_i(\alpha)}{I_i(\beta)},$$

where $I_i(\alpha)$ and $I_i(\beta)$ are the respective intensities of the lines $\alpha$ and $\beta$ in the element i.

In an emission spectrum of a sample, two types of lines may appear: atomic emission lines, which correspond to atoms in an excited state, and ionic emission lines, which correspond to ions in an excited state. The atomic lines are the ones that have the longest life and the greatest stability over time, which makes it possible to analyze them for a longer time. Thus, according to one embodiment of the invention, the emission lines of the sample that are taken into account are preferably the atomic emission lines.

In order to obtain the best possible analyses, whether for the creation of the database or for the analysis of the sample itself, it is necessary to use detection devices that cover the widest possible spectral range in order to measure the largest possible number of lines. To this end, in one embodiment of the invention, the optical emission spectroscopy analyses are performed using spectrometers that make it possible to simultaneously scan a spectral range spanning from at least 200 to 1000 nm.

However, it is also possible to use other types of detection devices to detect the emission lines present in the spectrum of the sample to be analyzed. These devices, for the most part, have behaviors that vary as a function of the wavelength along the entire width of the spectrum. It is therefore necessary, during the analysis, to take this behavior into account. To this end, in one embodiment of the invention, devices such as calibration lamps are used to determine a device function K, which represents the influence of the detection device on the measurement of the intensities of the lines as a function of the wavelengths of those lines. Calibration lamps are devices that send a known quantity of photons as a function of the wavelength to which they are subjected. Thus, by comparing the quantities of photons measured by the detection device with the known quantities, it is possible to determine the influence of the device on the measurements, as a function of the wavelengths. In the same embodiment, once the measurements are performed by a given device, the intensities of the various emission lines are multiplied by a compensation factor that depends on this device function K.

In one embodiment, the detection device used is such that its device function K is a constant. In that case, the compensation factor is equal to 1 for all of the lines.

In the case where two devices have the same device function K, it is possible to use the database directly, without taking this function K into account, since the influences of the devices on the measurements is the same, and thus has no effect on the calculations of the intensity ratio or the inter-element coefficients.

The various emission lines present in a spectrum have different energy levels, which correspond to higher or lower intensities. Low-intensity lines, known as less sensitive lines, are more difficult to measure at a given concentration, and for that reason it may be necessary to perform an acquisition for a relatively long time, for example 10 seconds, whereas for high-intensity lines, known as sensitive lines, 1 second is enough. Thus, in one embodiment, the analysis is performed by a detection device having variable and adjustable acquisition times. This makes it possible to chose times so as to detect at least a substantial number of the emission lines, whatever their sensitivity. Different acquisition times may also be required to determine the intra- and inter-element coefficients.

When a long acquisition time is used, the intensities of the sensitive rays will reach the saturation threshold of the device. This is not a problem when measuring the intensities of the less sensitive lines. However, when intending to calculate an intra-element coefficient, for example, it is necessary to make sure that the two lines taken into account in the coefficient do not become saturated. In one embodiment, depending on the measurement performed, the acquisition times are adjusted so that certain intensities do not reach the saturation threshold of the detection device.

Once the detection has been performed with variable acquisition times, it is of course necessary to convert them to the same scale, in order to be able to make comparisons and to be able to use the database. To this end, in one embodiment, and particularly in the case of the quantitative analysis, the emission line intensities are normalized by dividing them by factors that depend on the acquisition times used. For example, the reference time may be considered to be one second. In that case, all of the measurements performed with an acquisition time equal to P seconds will be divided by a normalization coefficient equal to P.

As indicated above, one of the steps in the method for analyzing a sample consists of determining, from the emission spectrum, the elements present in the sample to be analyzed. To do this, the database created specifically for this analysis is used. This database contains, for a certain number of pure elements, the wavelengths and intensities of all of the lines. In order for the determination to be as exact as possible, it is necessary to have an exhaustive or near-exhaustive list of the elements present in the sample. Thus, using this base, the elements are determined, in one embodiment of the invention, using the following types of detection criteria:

the presence, in the spectrum of the sample to be analyzed, of more than X % of its emission rays, X preferably being equal to 50, and/or the presence, in the spectrum of the sample to be analyzed, of at least M lines from among the N most intense lines of the pure element, M preferably being equal to 3, and N preferably being between 5 and 10.

The criterion chosen may be the same for all the elements of a sample, or may be different depending on the element; an element may also be considered to be present in a sample when both of the criteria mentioned are met.

Other features and advantages of the invention will emerge from the nonlimiting description of one of its embodiments, this description being illustrated by FIG. 1, which represents a device used to perform a qualitative and quantitative analysis by means of a method according to the invention.

This device is used to perform an analysis on a sample in the liquid phase. This sample is contained in a reservoir 10. It is fed by peristaltic pumping (12) into a tube 16. The upper part of the tube is surrounded by a sheath 14 containing gaseous nitrogen that serves to confine the jet as described in international application WO 2004/029598. The sample descends through the tube 16 until it reaches an excitation zone 17. This zone corresponds to the place where the tube is hit by a laser beam 18. This laser beam 18 is reflected by a dichroic mirror made of molten silica 20 and passes through a lens 22 of focal length f equal to 30 cm, so as to reach the tube 16 with an angle of incidence inclined by about 15° from the horizontal. The laser beam 18 makes it possible to excite the sample located in the zone 17, which will then be transformed into plasma and will emit a light spectrum composed of lines having different wavelengths. This spectrum will pass through two lenses 22 and 24 with focal lengths respectively equal to 30 cm and 10 cm. This spectrum is then transmitted, via an optical fiber 26, to a detection device for acquiring the measurements.

Depending on the elements (the quantity, the sensitivity of the lines) to be analyzed, the solutions are recycled through the jet system for variable amounts of time.

The invention claimed is:

1. A method for qualitative and quantitative analysis of any type of single- or multi-element sample by optical emission spectroscopy with laser excitation, comprising the steps of:
    calculating inter-element coefficients between all elements of interest likely to be found together in a sample based on a qualitative analysis by a detection device, an inter-element coefficient corresponding to a ratio between intensities of two lines from two different elements, said inter-element coefficient being represented by the formula, $$coefficient_{(i,j)}(\alpha/\beta) = \frac{I_i(\alpha)}{I_j(\beta)},$$

where $I_i(\alpha)$ and $I_j(\beta)$ are the respective intensities of line $\alpha$ in element i and line $\beta$ in element j obtained from a database generated on single-element aqueous solutions all having the same pure element concentration, the database containing, for each element, the wavelengths of the emission lines and their respective intensities:
    analyzing the sample by the detection device using an optical emission spectroscopy to determine a plurality of emission lines present and their respective intensities to provide an emission spectrum by exciting the sample using a laser to transform the sample into a plasma;
    determining the elements present in the sample from the emission spectrum by the detection device; and
    quantitatively calculating respective concentrations of the elements identified previously during the qualitative analysis using the inter-element coefficients and the intensities of the emission lines detected by applying the following formula:

$$c_1 + \sum_i coefficient_{(1,i)}(\alpha_i/\beta_i) * \frac{J_i(\beta_i)}{J_1(\alpha_i)} * c_1 = 100,$$

in which $c_1$ represents mass percentage concentration of an element of the sample chosen as a reference element, and terms of the sum represent the concentrations of other elements identified in the sample expressed as a function of the concentration $c_1$, the inter-element coefficients, and the intensities Ji measured by the detection device during the analysis of the sample using the optical emission spectroscopy.

2. The method of claim 1, further comprising the step of analyzing the sample in liquid, solid or gaseous phase using the optical emission spectroscopy.

3. The method of claim 1, further comprising the step of calculating the inter-element coefficients by the detection device using the database generated from the pure element concentrations of the solutions that are lower than a predetermined value to prevent self-absorption of the lines that can alter the precision of the quantitative analysis.

4. The method of claim 1, further comprising the step of calculating the inter-element coefficients by the detection device using the database generated from the pure element concentrations of the solutions that are lower than 0.5% by mass to prevent self-absorption of the lines that can alter the precision of the quantitative analysis.

5. The method of claim 1, further comprising the steps of:
    determining when at least one emission line of the emission spectrum of the sample has reached a saturation threshold of a spectrometer performing the optical emission spectroscopy by the detection device; and
    reconstructing the intensity of said at least one emission line as a function of the intensities of other remaining emission lines belonging to the same element and as a function of pre-calculated intra-element coefficients by the detection device using the database, an intra-element coefficient corresponding to a ratio of the intensities of two emission lines of the same element represented by the formula:

$$coefficient_i(\alpha/\beta) = \frac{I_i(\alpha)}{I_i(\beta)},$$

where $I_i(\alpha)$ and $I_i(\beta)$ are the respective intensities of the lines $\alpha$ and $\beta$ in the element i.

6. The method of claim 1, further comprising the step of determining a plurality of atomic emission lines by the detection device using the optical emission spectroscopy.

7. The method of claim 1, further comprising the step of performing optical emission spectroscopy analyses by spectrometers to simultaneously scan a spectral range spanning from at least 200 to 1000 nm.

8. The method of claim 1, further comprising the steps of determining a device function K using calibration lamps, said device function K representing the influence of the detection device on the measurement of the intensities of said plurality of emission lines as a function of wavelengths of said plurality of emission lines and multiplying the intensities of said plurality of emission lines by a compensation factor based on said device function K.

9. The method of claim 8, wherein the device function K of the detection device is constant; and wherein the step of multiplying the intensities uses the compensation factor equal 1 for all emission lines.

10. The method of claim 9, further comprising the step of normalizing the emission line intensities by dividing the emission line intensities by factors based on the selected acquisition times by the detection device to perform the quantitative analysis.

11. The method of claim 1, further comprising the step of analyzing the sample by a spectrometer having variable and adjustable acquisition times to perform the optical emission spectroscopy to select acquisition times that enables the detection device to detect a large number of emission lines regardless of their sensitivity.

12. The method of claim 11, further comprising the step of adjusting the acquisition times so one or more emission line intensities do not reach a saturation threshold of the spectrometer.

13. The method of claim 1, further comprising the step of utilizing following types of detection criteria by the detection device to determine the elements present in a sample to be analyzed from the emission spectrum: the presence of more than X % of emission rays in the spectrum of the sample to be analyzed, wherein X is equal to 50, or the presence of at least M lines from among N most intense lines of the pure element in the spectrum of the sample to be analyzed, wherein M is equal to 3 and N is between 5 and 10.

* * * * *